United States Patent [19]

Stout et al.

[11] Patent Number: 4,986,908
[45] Date of Patent: Jan. 22, 1991

[54] ORGANIC-BASED POROUS MICROSPHERES FOR HPLC

[75] Inventors: Richard W. Stout; Henry J. Leibu, both of Wilmington, Del.

[73] Assignee: E. I. du Pont de Nemours and Company, Wilmington, Del.

[21] Appl. No.: 390,440

[22] Filed: Jul. 31, 1989

Related U.S. Application Data

[60] Division of Ser. No. 315,297, Feb. 24, 1989, Pat. No. 4,902,413, and a continuation of Ser. No. 191,220, May 6, 1988, abandoned.

[51] Int. Cl.$^5$ .............................................. B01D 15/08
[52] U.S. Cl. .............................. 210/198.2; 210/502.1; 210/635; 210/656; 502/402; 502/439; 521/56; 521/76; 521/188
[58] Field of Search ............... 210/635, 656, 657, 658, 210/659, 198.2, 502.1; 502/401, 402; 521/56, 76, 188; 525/509; 528/232

[56] References Cited

U.S. PATENT DOCUMENTS

| | | | |
|---|---|---|---|
| 2,408,986 | 10/1946 | Marisic et al. | 252/259.3 |
| 3,275,576 | 9/1966 | Flodin et al. | 260/2.2 |
| 3,652,540 | 3/1972 | Determann et al. | 260/232 A |
| 3,910,848 | 10/1975 | Froehlich | 252/90 |
| 3,928,272 | 12/1975 | Brancato | 162/166 |
| 3,931,063 | 1/1976 | Renner | 521/63 |
| 4,010,242 | 3/1977 | Iler et al. | 423/335 |
| 4,045,353 | 8/1977 | Kosaka et al. | 210/502 |
| 4,094,833 | 6/1978 | Johansson et al. | 260/17.4 |
| 4,685,930 | 8/1987 | Kasprzak | 252/153 |
| 4,687,814 | 8/1987 | Chaumont et al. | 525/242 |

FOREIGN PATENT DOCUMENTS 8301453 4/1983 PCT Int'l Appl. ............... 2/16

OTHER PUBLICATIONS

Perry's Chemical Engineering Handbook, 4th Edition, McGraw-Hill Book Co., New York, 1963, pp. (16-16)-(16-19).
Ito et al., Journal of Chromatography, 333:107-114 (1985).
Kato et al., Journal of Chromatography, 333:96-106 (1985).
Hirata et al., Journal of Chromatography, 396:115-120 (1987).
Hjerten et al., Journal of Chromatography, 396:101-113 36 (1981).
Porath, Journal of Chromatography, 218:241-259 (1981).
Dawkins et al., Journal of Chromatography, vol. 371, 283-291 (1986).

Primary Examiner—Ernest G. Therkorn

[57] ABSTRACT

Porous organic microspheres for use in HPLC are formed by coacervating a colloidal silica sol in a uniform mixture of the sol and a polymerizable organic material. The silica particles which formed the sol are removed from the microspheres with ammonium bifluoride. The remaining organic microspheres are rigid, have uniform pore sizes and distribution, and do not swell or shrink in the presence of the solvents used in HPLC.

13 Claims, 7 Drawing Sheets

ORGANIC-BASED POROUS MICROSPHERES FOR HPLC

This application is a continuation Ser .No. 07/191,220 filed May 6, 1988, now abandoned, and a division of Ser. No. 315,297 filed Feb. 24, 1989, now U.S. Pat. No. 4,902,413.

FIELD OF THE INVENTION

This invention relates to packing materials for high performance liquid chromatography and processes for their manufacture.

BACKGROUND OF THE INVENTION

High performance liquid chromatography (HPLC) is a very versatile technique used for the separation and purification of a wide variety of organic and inorganic substances. HPLC has been well described by Snyder and Kirkland in an "Introduction to Modern Liquid Chromatography," Snyder, L. R., and Kirkland, J. J., 2nd Ed., Wiley Interscience, N.Y. (1979). It differs from classic chromatographic methods in the size and nature of the packing materials. HPLC uses packing materials which have particle sizes int he range of 5 to 10 μm and in which the particles are generally very porous. HPLC can be carried out in several modes; and they are, absorption of a compound of interest using polar supports (normal phase), absorption of the compound of interest with nonpolar supports (reversed phase), electrostatic interactions (ion exchange), ion pairing interaction (mixed absorption modes), size exclusion (separation based on molecular size), and affinity (biospecific binding).

The ideal support for HPLC would be a material that is extremely rigid, has a coefficient of cubic expansion of essentially zero under normal operating temperatures and has a suitable surface for further chemical derivatization. It would have a controlled geometry, that is, it would be spherical, have a monodispersed particle size distribution with controlled pore size. It would have appropriate surface properties for the intended chromatographic separation mode. And it would be inexpensive to manufacture.

The currently used HPLC packings may be broadly classified in two categories, one being organic based supports and the other being the inorganic-based supports. Silica gel and, in limited cases, alumina are preferred materials for inorganic-based supports. Silica gel may be used for chromatographic purposes without further surface modification, or the surface may be coated or chemically modified with organo silanes or other substances to offer the desired surface properties.

The advantage of an inorganic support, and particularly silica gel, is that it is a rigid material and can withstand pumping pressures of 10,000 to 15,000 psi and has a suitable surface for further chemical derivatization (silanol groups). It has controlled geometry and is relatively inexpensive to manufacture.

Marisi et al. describe in U.S. Pat. No. 2,408,986 a gel bead used as a catalyst. The beads are formed by increasing the pore size of inorganic gels by dispersion with finely divided combustible materials of 300 mesh size and smaller in gelable solutions. After gelation, the hydrogel is purified, dried, and the combustion material removed by oxidation to form pores larger than those present in the original gel structure.

The inorganic-based supports suffer from the disadvantages that when working with large biochemical molecules it is very difficult to eliminate the undesired interactions of the biomolecules with the modified silica surfaces. Also, in the pH range where most biochemical separations are performed the silica based supports tend to be unstable. Therefore, organic substances are widely used as HPLC supports in biochemical steudies. Organic supports can frequently be manufactured to have little or no undesirable interactions between the desired solute and the support. However, organic supports often have lower rigidity which results in lower maximum pumping pressures that could otherwise be used (~5,000 psi for the hard gels and ~200 psi for the soft gels).

There are many examples in the art of processes for making various organic based supports. In U.S. Pat. No. 3,275,576 issued Sept. 27, 1966 to Flodkin et al. there is disclosed a process for preparing substitution products of hydrophilic high molecular weight copolymerizates of aliphatic hydroxyl group-containing substances with bifunctional organic substances. The products are obtained by reacting the hydroxyl groups of the copolymerizates with a monofunctional substance and are useful as cation-exchangers in separations. There is no disclosure by Flodkin et al. that these gels might have unusually high rigidity and therefore be able to withstand unusually high (for organic supports) pumping pressures.

In U.S. Pat. No. 3,652,540 issued Mar. 28, 1972, Determan et al. discloses a process for making ion exchangers which have as their base rounded particles of regenerated cellulose. These resins have improved flow properties over microcrystalline cellulose based materials but still suffer from resin compaction and reduced flow rates under higher pressures.

Kokaka et al. (U.S. Pat. No. 4,045,353 issued Aug. 30, 1977) disclose a process for producing chromatographic supports which have a microporous inorganic support and a radiation polymerized organic coating which has part of the polymer grafted to the surface of the inorganic support and a part of the polymer not bonded to the support. Kosaka et al. do not remove the inorganic core from the polymer prior to use as a chromatographic support.

U.S. Pat. No. 4,094,833 issued June 13, 1978 to Johansson et al. discloses a process for producing an improved dextran gel in particle form which has a much higher pore size and rigidity than previous dextran gels. This is accomplished by using a divinyl compound in the copolymerization reaction. Although this dextran has higher rigidity and improved flow properties over previous dextran gels it still is not suitable for use in HPLC applications.

Naofumi et al. [Journal of Chromatography 333, 107-114 (1984)] disclose the use of a polyvinyl alcohol gel to which benzamidine had been covalently linked for the separation of trypsin. Naofumi et al. achieve a flow rate of 1.7 mL per minute with a pressure drop n the column of less than 356 psi. The gel particles they used had a narrow-sized distribution of $9 \pm 0.5$ micrometers.

Kato et al. [Journal of Chromatography 333, 93-106 (1985)] report the use of a hydrophilic resin-based support for the reversed phase chromatography of proteins. Their support was developed by introducing phenol groups with an ether linkage into TSK gel G5000 pw. They report this material to be effective for the reverse phase chromatography of proteins using flow rates in the range of 0.5 to 1.5 mL per minute.

Hirata et al. [Journal of Chromatography, 396, 115–120 (1987)] discuss the performance of Asahipak GS columns (hydrophilic gels of vinyl alcohol copolymer) when exposed to various organic solvents. In all cases the use of organic solvents affects either swelling or shrinking in the gels. This is a very undesirable property for supports for use in HPLC.

Hjerten et al. [Journal of Chromatography 396, 101–113 (1987)] disclose a chromatographic support based on agarose crosslinked with divinyl sulphone. This support has enhanced rigidity compared to standard agarose but still can only withstanding pumping pressures up to 580 psi.

Porath [Journal of Chromatography 218, 241–259 36 (1981)] describes a process for preparing crosslinked agarose which has a higher rigidity than standard agarose. This process involves including particles that can be dissolved under conditions that do not disturb agarose (in a low agarose content gel). The gel is then contracted by washing with a suitable organic solvent followed by drying. The gel is then crosslinked in a solvent which does not re-swell the gel. The particles are then dissolved leaving a porous, crosslinked agarose. Porath does not discuss the pressures that these crosslinked agaroses can withstand without collapsing.

Most of the prior art appears to each producing porous microspheres from vinyl monomers using emulsion or suspension polymerization techniques such as:

| | |
|---|---|
| Styrene - divinyl benzene | |
| Acrylonitrile-divinyl benzene | (JOC 358 (1986) 129–136) |
| Vinyl pyridine | (JOC 354 (1986) 211–217) |
| Vinyl alcohol | (JOC 349 (1985) 323–329) |
| Glycidyl methacrylate | (JOC 376 (1986) 269–272) |

JOC = Journal of Chromatography

These processes produce spherical polydisperse particle sizes and the mean particle size depends on the ratio of water to organic solvent, concentration and type of emulsifiers, rate of stirring, time, temperature, relative solubilities of reactants in aqueous and organic phases, and the nature and solubility of free radical generators. The matter is further complicated by trying to introduce pores of desired shape and size into the polymer matrix. This is usually accomplished by adding an inert substance (such as toluene) which is incorporated into the organic sphere but does not participate in the polymerization process. These processes are very tedious and the final results depend on a host of variables as noted above.

Another factor is the inherent linear nature of the vinyl copolymers in which crosslinking is introduced to add mechanical strength (usually divinyl benzene). These linear polymers, based on vinyl copolymers, tend to swell in organic solvents. This is a severe problem since the nature of the packed bed will change when exposed to different liquids causing changes in column permeability, back pressure, etc.

Monodispersed microspheres may be produced by swelling latex particles as described by Uglestadt et al. in PCT application NO 82/00052 published Apr. 28, 1983, Publication No. WO 83/01453. How to introduce pores in these materials is not taught. The process depends critically on the relative solubility of the monomers and polymers in water and organic phases and is sensitive to temperature, stirring, time and temperature.

Some of the prior art is based on crosslinked agarose. These materials are very sensitive to swelling in organic solvents, are very soft and unsuitable for HPLC.

In U.S. Pat. No. 4,010,242 issued Mar. 1, 1977 Iler et al. disclose a method of making uniform, porous oxide microspheres by forming a mixture of urea or melamine and formaldehyde in an aqueous sol containing colloidal oxide particles, copolymerizing the organic constituents and then burning out the organic constituent. Iler et al. do not discuss the possibility of dissolving the oxide particles after the copolymerization step to give a porous organic copolymer useful as a support in chromatographic separations.

The organic-based supports described to date generally suffer from a number of deficiencies as described above. In particular, They have insufficient rigidity and they will swell or shrink in organic solvents. Both of these properties cause the HPLC supports to collapse under high pumping pressures or gradients of varying organic solvent concentration. These problems reduce their chromatographic efficiency and render the supports useless for further chromatographic separations.

SUMMARY OF THE INVENTION

According to this invention, there is provided a process for forming uniform-sized, porous organic microparticles that overcome many of the disadvantages of the known organic based supports. This process comprises the steps of:

a. forming a sol of inorganic colloidal particles in a polar liquid, the colloidal particles having a hydroxylated surface and being dispersible in said polar liquid;

b. forming a mixture of the sol with a polymerizable organic material comprising formaldehyde and a second organic material selected from the group consisting of urea and melamine;

c. initiating polymerization of the organic material in said mixture to cause coacervation of the organic material and said colloidal particles into microparticles having a diameter of about 0.5 to about 20 microns;

d. solidifying the microparticles so formed; and e. subjecting the microparticles so formed to a solution of a reagent of suitable composition and of sufficient strength to dissolve all of the inorganic component.

The resulting organic microparticles may be collected, washed and dried to form a powder. When the organic microparticles are urea formaldehyde, their surface has alcohol groups which are derivatized. Derivatization is accomplished by use of one of the groups consisting of chloroformates, isocyanates, and iodoacetates to form carbamates.

The powder comprises a plurality of porous, substantially uniform-sized similar to the size uniformity of the inorganic microspheres described by Iler et al., microspheres having an average diameter by number of from 0.5 to 20 microns, the said microspheres being an organic copolymer (a) selected from the group consisting of urea formaldehyde and melamine formaldehyde and (b) defining pores arranged in a uniform three dimensional lattice. The microspheres preferably have a derivatized surface to which is attached functional groups useful in HPLC separations.

The microspheres have a density and uniform pore distribution the uniformities of which are a function of the uniformity of the sol and organic materials mixture prior to the polymerization. A highly uniform mixture produces microspheres with a corresponding highly uniform density and pore size distribution. They are rigid enough to permit their use for HPLC and essentially do not well or shrink in organic solvents. They are easily derivatized and various functional groups may be attached to permit their use n different forms of HPLC.

When so used in chromatographic separation the microparticles comprise a region through which materials to be separated are passed. The improvement of this invention is that the microparticles comprise a plurality of uniform-sized porous microspheres having an average diameter of about 0.5 to about 20 microns, substantially all of said microspheres having a diameter ranging from about 0.5 to about 1.5 times the average diameter of the microspheres, the said microspheres being an organic copolymer (a) selected from the group consisting of urea formaldehyde and melamine formaldehyde and (b) defining pores arranged in a uniform three dimensional lattice.

A process for performing chromatographic separation comprising contacting the materials to be separated in a carrier phase with a resolving zone, the improvement wherein said resolving zone comprises a plurality of uniform-sized porous microspheres having an average diameter of about 0.5 to about 20 microns, the said microspheres being an organic copolymer (a) selected from the group consisting of urea formaldehyde and melamine formaldehyde and (b) defining pores arranged in a uniform three dimensional lattice.

The powder produced by the relative simple process of this invention has a controlled porosity that can be used for normal phase, reversed phase, ion exchange, mixed absorption mode, size exclusion and affinity HPLC chromatography. It is highly rigid, essentially not affected by organic solvents, and has a surface suitable for further chemical derivatization. The microparticles are spherical and the porosity, pore size, and pore size distribution are controllable and the microparticle size is essentially monodispersed. The microspheres do not require the use of vinyl compounds.

BRIEF DESCRIPTION OF THE DRAWINGS

Further advantages and features of this invention will become apparent from the following description wherein.

DETAILED DESCRIPTION OF THE PREFERRED EMBODIMENT OF THE INVENTION

In the present invention, microparticles of urea formaldehyde and silica preferably are formed by the coacervation process described by Iler et al. in U.S. Pat. No. 3,855,172, the contents of which patent are incorporated herein by reference. In this process, colloidal silica gel particles are used to form a coacervate (aggregate of silica and urea formaldehyde copolymer) with urea, formaldehyde and acid. It was originally believed by Iler et al. that the urea formaldehyde, silica coacervate was solid and the organic portion had no utility but was to be burned out to leave behind oxide microparticles. Surprisingly, according to this invention, the urea formaldehyde coacervate can be made porous by removing the inorganic component, i.e., the silica. When the silica is removed by a compound such as ammonium bifluoride, the resultant organic microparticles are very firm, porous and work well as chromatographic supports. These organic microparticles are monodispersed with pore size and porosity features, including uniform pore distribution, well controlled.

In preparing the porous, organic microparticles of this invention, it is essential to be able to control physical parameters which determine performance of these microparticles when used, in chromatographic packings. These critical, parameters are particle diameter, pore size diameter, pore volume, pore configuration, density distribution, and pore size distribution.

Simply stated, all that is necessary to control pore size is to add inorganic sol particles of a selected size prior to the polymerization step. The uniformity of the sol particle sizes determine the uniformity of the pore sizes. Microparticle diameter can be controlled by adjusting the concentrations of monomer or comonomers. In the preferred embodiment of the instant invention, the pore size is controlled by varying the size of the silica particle used to make the sol and the particle size would be controlled by varying the amounts of urea and formaldehyde present in the copolymerization step. Uniformity of pore size is a function of the uniformity of the sizes of the colloidal silica. It is a matter of simple optimization given the teachings of the instant invention and those of Iler et al. for one, skilled in the art to determine the conditions necessary to produce porous organic microparticles, over a large range of particle sizes and pore sizes, having a desired degree of uniformity of both particle size and pore distribution.

Figure 7:
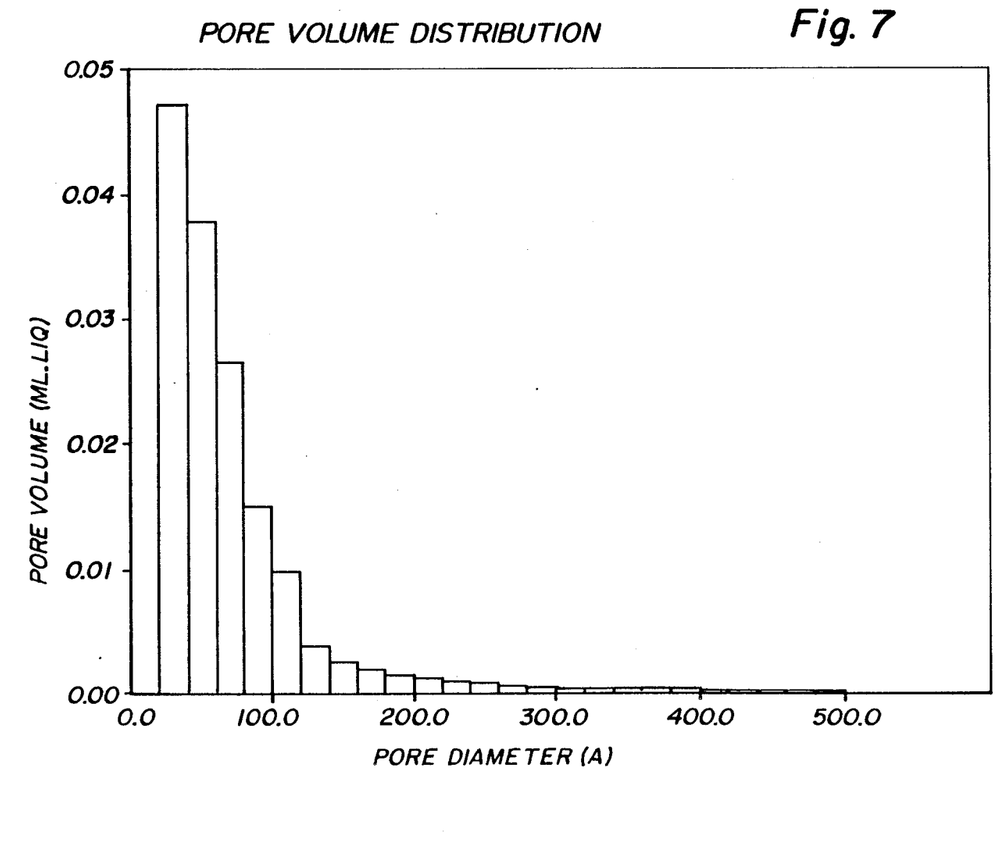
FIG. 7 is plot depicting pore volume distribution of the microparticles of this invention in which pore volume is plotted as the ordinant and pore diameter as the obscissa.

It should noted that porous urea-formaldehyde microparticles typically are in the form of microspheres. Also the microspheres can be made without the use of an inorganic component but the resulting pore volume is small, i.e., about twenty percent (20%). However, the use of silica sol allows much better control of and range of pore size and is, therefore, the preferred mode. FIG. 7 shows a pore volume distribution from a typical UF microsphere in which 5.5 nm silica sol, with the colloidal particles ranging 5.5 nm ±2.0 nm, was used to define the pore size. In contrast to other methods of introducing pores into organic spheres by the liquid inert substances (like toluene) the pore volume distribution closely follow the sol from which it was made, e.g., 55Å±20 A constituting the bulk of the pore volume. There are no sporadic volumes outside of the mean sol diameter of consequence but rather gradual diminishing pore volume fractions as the pore size diameter exceeds 100Å. It can be seen that pore size is uniform in the UF microspheres of this invention.

The organic components useful in the present invention ar the same as disclosed by Iler et al. (supra), that is copolymers of urea and formaldehyde or melamine and formaldehyde.

The inorganic component of the microparticle must be selected so that it can be dissolved using reagent that do not adversely affect the organic component. When using silica sols, ammonium bifluoride is the preferred dissolving reagent. Other known reagents may be used and will be apparent to the skilled artisan.

The porous organic microspheres of the instant invention can be surface modified by any known chemistry to provide surface characteristics suitable for a variety of chromatographic applications such as ion exchange, size exclusion and the like. These modifications are accomplished by first introducing an organic functional group covalently attached to the UF surface.

The surface chemistry of the preferred urea-formaldehyde (UF) porous microspheres is controversial and complicated. It appears that the surface contains alcohol groups and substituted ureas. One method of chemically altering the UF surface is to derivatize the alcohol groups ($-NH-CH_2-OH$). There are several reagents which can be used for this purpose of which three (chloroformates, isocyanates and iodoacetate) have been studied for application to this invention. It should be readily recognized by one skilled in the art that many other reagents (anhydrides, cyanogen bromide, and acid halides) could be used.

Chloroformates react with alcohols to form activated esters which then react with primary amines ($R-CH_2-NH_2$) to form carbamates. The primary amine can be substituted with additional functional groups of interest, such as a polyamine, alcohol, ester, or other group. The functional group can then be chemically modified in additional chemical reactions to provide any variety of surface desired. Reactions of this type are well known in the art.

Isocyanates react directly with alcohols to form carbamates. Either of the chloroformate or isocyanate reactions will function in the instant invention, however, the chloroformates reaction is preferred since there is more flexibility in selecting the functional group because some isocyanates will react with some functional groups ($-OH$, $NH_2$) and form polymers.

The alcohol groups may be attacked by other reagents such as iodoacetate which is preferred. This reaction forms carboxylic acids which can then be used as they are for cation exchange chromatography or they can be further reacted with derivatizing agents such as 1,1'-carbonyldiimidazole (CDI) or 1-(3-Dimethylaminopropyl)-3-ethyl carbodiimide (EDCI). Reactions of this type are well known in the art. The derivatives can then be reacted with primary amines to form substituted carbamates.

The amide groups on the surface may be reduced to primary amines by the use of lithium aluminum hydride (LAH) in dry solvents. The resultant surface chemistry is unknown but apparently includes primary alcohols and amines. Reagents described above, will then react with either or both of these groups, thus allowing covalent attachment of functional groups of interest. Other groups may be introduced on the UF surface by reducing agents such as lithium aluminum hydride. This reaction with UF microspheres presumably produces amines on the surface which may then react with reagents specific form amines.

Standard column packing techniques can be used with the porous organic microspheres of the instant invention. When the preferred urea-formaldehyde porous microspheres are used, packed columns are readily obtained. First, the quantity of microspheres is selected based on the dimensions of the column. The microspheres are then slurried in a minimum volume of water just sufficient to form a thick slurry. Aliquots of the slurry are transferred to an empty column blank. The blank is filled nearly to the top with the slurry. The fitting are connected to the column blank and a pump is used to push the microspheres toward the bottom of the column blank. The pumping is stopped, the inlet fitting of the column is removed and excess liquid, devoid of microspheres, is removed using a pipet. More slurry is added, the fitting on the column inlet is connected and pumping is resumed. The process of opening the column, removing the excess liquid, and adding more slurry is repeated until the column is full. The inlet fitting is then replaced, secured and the column is ready for operation.

Alternately, UF microspheres produced by this invention may be high pressure slurry packed into column blanks of pressures ranging from 2000–8000 psi as described by Snyder and Kirkland (Introduction to Modern Liquid Chromatography), Wiley-Interscience, N.Y., 1984, pp. 191 to 193).

For the sake of completeness, the coacervation process for preparing microparticles as described by Iler et al. is set forth. A sol containing inorganic colloidal particles in a polar liquid is first prepared. The sol is normally an aqueous sol but it can be a mixture of water and other non-effecting liquid materials, or even a nonaqueous polar liquid. The primary considerations are that the colloidal particles are relatively insoluble and dispersible in the polar liquid; that the organic material is initially sufficiently miscible in the polar liquid to form a uniform mixture; and that the organic material will polymerize in the polar liquid at one stage to form a coacervate. Under normal circumstances, the sol will be an aqueous sol, and for convenience, the discussion which follows will be limited to that situation.

The formation of the microparticles proceeds by association of the inorganic colloidal particle with the organic coacervate. It is postulated that the extreme uniformity in both the size of the microparticles and the distribution of the colloidal particles within the microparticle depends on an interaction between hydroxyl groups on the surface of the particle and portions of the polymer chain. For this reason, at least prior to the onset of polymerization, the colloidal particles must have hydroxyl groups on their surfaces equivalent to a hydrated oxide surface. The interior of the microparticles may consist of other particles but the surface must be capable of being hydroxylated.

To begin with, then, the inorganic material used in the present invention must be an oxide or oxide coated material, i.e., one that develops a hydroxylated surface. However, to be useful in the present invention, the inorganic material must be present as surface-hydroxylated particles of colloidal size which are insoluble and colloidally dispersed in the medium required for the polymerization of the organic material used; in particular, an acidic medium containing urea formaldehyde or melamine formaldehyde. Thus water-insoluble, acid-insoluble oxides can be used. Normally, oxides of metals are preferred so any water-insoluble, acid-insoluble oxide of groups IIIB, IVB, VB, and VIB of the Periodic Table, as well as those of silicon, germanium, tin, antimony and bismuth may be used. A water-soluble higher oxide of chromium, e.g., chromium trioxide, is unsuitable, but, the lower oxide $Cr_2O_3$ which forms relatively acid-resistant colloidal particles, may be used. In the same manner, those oxides of the rare earth elements which remain undissolved at room temperature for a period of several hours at pH$^2$ may be used. On the other hand, the basic types of finely-divided form will pass into solution slowly, must be polymerized with the organic components at maximum feasible pH to coprecipitate the oxide with the organic polymer before the acidic medium dissolves the metal oxide; here melamine-formaldehyde is preferred.

The ultimate particles of the present invention must be colloidal in size. For the purpose of the present invention, this means that at least two of the dimensions of the ultimate particle must be in the range of 5 to 500 millimicrons (nanometers) and the other dimension must be int he range of 5 to 1,000 millimicrons (nanometers).

Particles having one dimension larger than about a micron are difficult to incorporate with organic polymers into spheres, because the spheres which generally form are only a few microns in diameter and large particles interefere with the formation of such discrete spherical units. Thus, some clays such as kaoline consisting of platelets 20 to 40 microns in diameter and 5 microns thick, do not form the spherical composite particles of this invention. Although the clay particles which are precipitated along with the urea formaldehyde polymer are intimately associated with the polymer, the product does not consist of uniform spheres, but masses of irregular shape. Similarly, asbestos fibrils which are only about 50 nm in diameter, but are longer than 1,000 nm, tend to give only irregular masses when coprecipitated with the urea formaldehyde polymer. However, if these materials are reduced in particle size, and especially if they are treated to ensure that the surface is siliceous, then they may be used in the process of this invention.

The particle size and shape of the inorganic colloidal particles, therefore, are limited to more or less isodimensional particles or rod-shaped particles. Leaflike colloidal particles give rise to very fine irregular shaped microparticles while more or less spherical colloidal particles give rise to spherical microparticles. Generally colloidal particles with dimensions greater than about 0.1 times the diameter of the microsphere or greater than 1,000 millimicrons in one direction or with more than one dimension greater than 500 millimicrons do not give uniform-sized particles.

The organic components must be soluble in the polar liquid, which generally means they must be water soluble and miscible with the inorganic colloidal particles without flocculating or dissolving them at the pH at which the reaction occurs; which in the case of urea or melamine and formaldehyde, this is at a pH of 2 to 6. The polymer in the course of formation must combine with the inorganic colloidal particles to form a coacervate which appears as rounded droplets which then harden as polymerization is completed.

Coacervation of the organic components and the colloidal particles into uniform-sized microparticles in which the colloidal particles are uniformly distributed, appears to require more than mere mechanical entrapment of the colloidal particles in the polymerizing material. To achieve the high degree of uniformity in both microparticle size and colloidal particle distribution (and hence pore distribution in the final powder) within the microparticle, some interaction between the oxide surface of the colloidal particles and the polymer chain appear to be involved. The highest degree of uniformity in both of these features appears to be dependent upon the use of a copolymerizing mixture of urea and formaldehyde, in mol ratio of about 1 to about 1.2 or 1.5 and a pH of about 1.0 to about 4.5, or a copolymerizing mixture of melamine and formaldehyde, in mol ratio of about 1 to about 3 and a pH of about 4 to about 6.

The ratio of the organic material to the inorganic material should be such that, after polymerization, the precipitated particles contain from about 10 to about 90% by weight of the inorganic component. This depends to some extent upon the relative density of the organic and inorganic components. The composition can also be expressed as percentage by volume of the components in the microparticle. The percent by volume of the inorganic component of the microparticle will usually range from about 10 to bout 50%, although up to about 70% is theoretically possible. The microparticles consist of a spherical mass of polymer in which the colloidal particles are embedded.

Initially, very fine copolymer particles are formed and these grow as polymerization progresses. Under some conditions, one family will grow to 10 microns and then a second family of smaller particles will form. Surfactants and water miscible solvents may be added to modify the size of the microparticles produced.

The microparticles obtained in the suspension or as a precipitate when the organic components are polymerized in a suspension or sol of inorganic colloidal particles, consists of a matrix of polymer forming a sphere within which the inorganic particles are embedded.

The organic microspheres (microparticles) are removed from the resulting slurry or suspension as by filtering thus forming a filter cake. This cake is washed several times in first water and then a suitable organic solvent useful to remove the water such as methanol and then dried by conventional means. The dried product is slurried in a chemical solution needed to dissolve the inorganic colloidal particles (this preferably is ammonium bifluoride in the case of silica). The UF product is filtered, washed with water (and dried if desired). The UF microparticles are slurry packed as desired in a chromatograph column as described.

EXAMPLE I

Synthesis of Porous UP Microspheres 12.55 g of a silica sol (Nalcoag ® 1060, specific surface area 60 m$^2$/g sol diameter 46 nm) containing 6.0 g of SiO$_2$ was placed in a 200 mL beaker. Distilled water was added for a final volume of 96 mL, then 3.0 g of urea was added and dissolved. Using a pH meter, a small quantity of concentrated nitric acid was used to adjust the pH to 1.0. The mixture was stirred rapidly and 4.06 g of 37% formaldehyde solution was quickly added. Stirring was allowed to continue for 10 seconds to thoroughly mix the contents of the beaker. The stirring was stopped and the solution allowed to stand undisturbed at ambient temperature for 30 min. White microspheres could be seen to settle to the bottom of the beaker at this point.

The slurry was filtered using a vacuum flask and a M-15 sintered glass funnel. A white cake of urea-formaldehyde-silica microspheres was observed. This cake was washed three times with 100 mL of water, then washed twice with 100 mL of methanol and finally washed twice with 50 mL of Freon ® TP (Du Pont). The cake was air dried in the filter for 30 min. and placed in a vacuum oven at 110° C., 24" Hg for 30 min.

The powder product weighed 9.39 grams which represents a 97% yield for the silica and a 99% yield for the urea-formaldehyde copolymer. Elemental analysis (based on % Ash) indicated that the product was 61.99% $SiO_2$ and 38.01% urea-formaldehyde copolymer.

The product above was then slurried in 200 mL of water and an equal weight of ammonium bifluoride [$NH_4(HF_2)$] was added. The mixture was stirred to dissolve the salt and allowed to stand for 20 min. The product was filtered and washed with 200 mL of water, and the process repeated twice more to ensure all of the $SiO_2$ was dissolved. Subsequent elemental analysis showed the % Ash to be less than 0.03%. Microscopic analysis indicted a plurality of spherical microparticles of about 5.0 micron mean particle diameter.

The percent weight of the silica, and hence the porosity, can be varied continuously from 6% to 70% by adding a quantity of silica sol in the range from 0.6 g to 18.83 g. The pore size can be independently varied from 5 nm to 400 nm by using the same method listed above and substituting sols of various sizes Table 1 lists sols that will produce UF microspheres with various pore sizes.

TABLE 1

| Sol Used | Specific Surface Area ($m^2/g$) | Diameter (nm) | Approximate Pore Diameter (nm) |
| --- | --- | --- | --- |
| Ludox ® LS | 160 | 17 | 19 |
| Ludox ® TM | 124 | 22 | 24 |
| Nalcoag ® 1115 | 493 | 5.5 | 7 |
| Nalcoag ® 1060 | 60 | 46 | 50 |
| Nalcoag ® 209 | 210 | 13 | 15 |
| Nalcoag ® 1030 | 230 | 13 | 15 |
| Nyacol ® 2040 | 126 | 21.6 | 24 |

EXAMPLE II

Size Exclusion Chromatography of Polystyrene Molecular Weight Standards Using UF Microspheres 15 g of UF microspheres were produced by a process similar to Example 1 except a nominal 13 nm particle diameter sol (Nalcoag ® 1030) was used. The UF microspheres were high pressure slurry packed using a method cited by Kirkland (Introduction to Modern Liquid Chromatography, Wiley-Interscience, N.Y., 1974, pages 191-192). The UF microspheres were slurried in methanol and pumped with methanol at an inlet pressure of 2000 psi. The column dimensions were 9.4 mm i.d., and 250 mm length.

The liquid chromatograph was an E. I. du Pont de Nemours and Company model 8800. The system pumped neat tetrahydrofuran (THF) at a flow rate of 1.0 $cm^3$/min. The at of size exclusion chromatography (SEC) is well known (Yau, Kirkland, and Bly, Modern Size-Exclusion Chromatography, Wiley-Interscience, N.Y., 1979). A contrived sample of polystyrene molecular weight standards (PSMW), (1,800,000; 17,500; 2000; plus toluene 92 daltons) was used. The concentration of each species was approximately 1 mg/mL.

Figure 1:
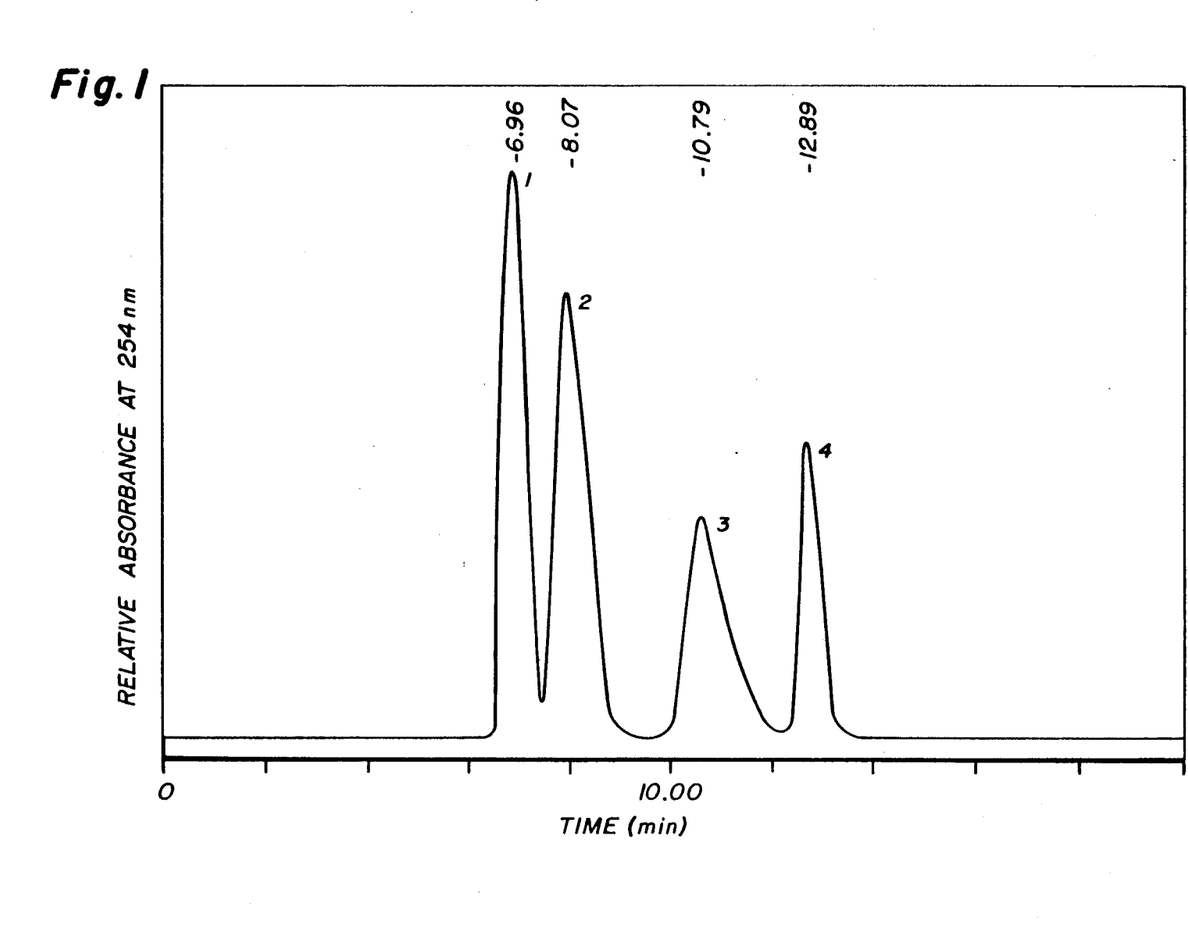
FIG. 1 is a chromatograph of molecular weight standards using the urea-formaldehyde microspheres produced in Example II.

The chromatographic system was operated in the isocratic mode and 5 μL of the contrived sample was injected. The resultant chromatogram is shown in FIG. 1. This illustrates that conventional chromatography in the SEC mode can be performed using porous UF microspheres made using the process of this invention.

Table 2 lists PSMW values, retention volume ($V_R$) and the Distribution Coefficient ($K_D$) (defined in Example III) for each standard for the chromatograph shown in FIG. 1.

TABLE 2

| Peak | PSMW (Daltons) | $V_R$ $cm^3$ | $K_D$ |
| --- | --- | --- | --- |
| 1 | 1,800,000 | 6.96 | 0.000 |
| 2 | 17,500 | 8.07 | 0.184 |
| 3 | 2,000 | 10.79 | 0.636 |
| 4 | 92* | 12.89 | 1.000 |

*Toluene to mark $V_m$.

EXAMPLE III

Control of Pore Size of UF Microspheres

Figure 2:
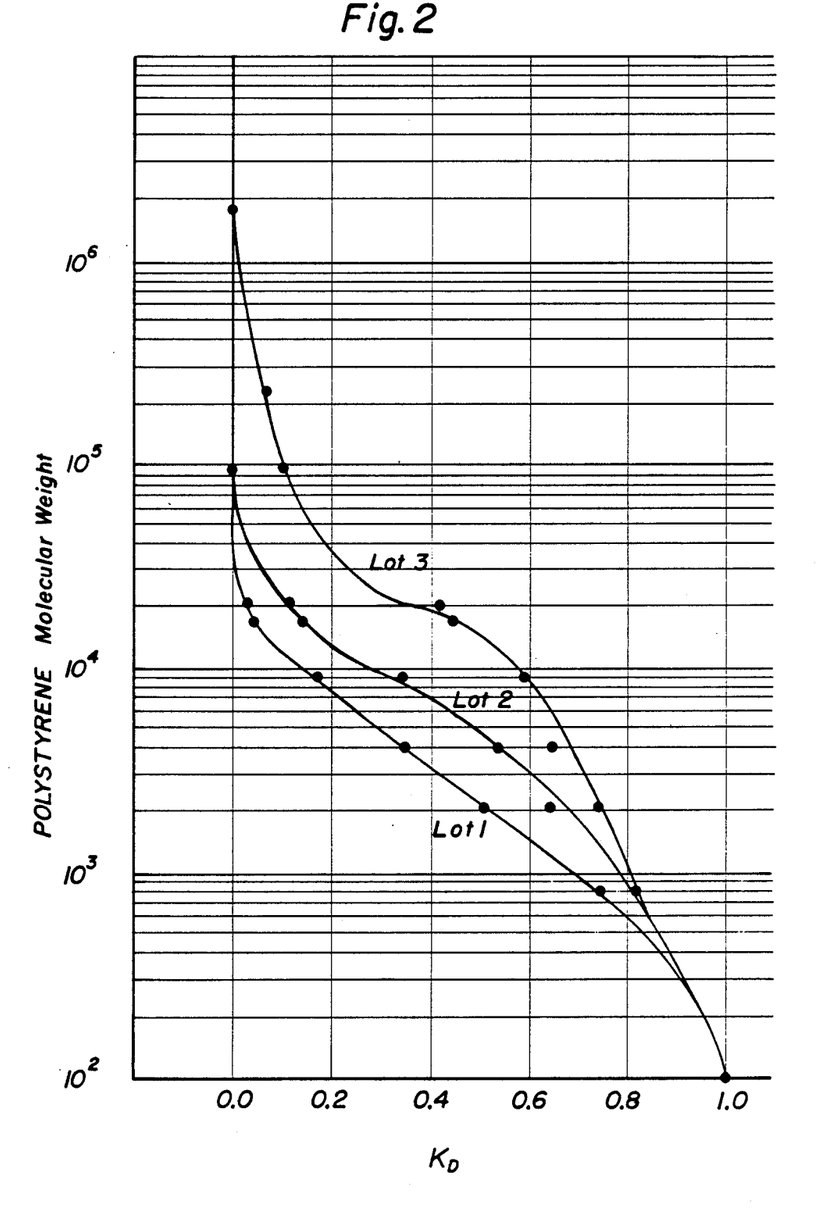
FIG. 2 is a graph of molecular weight versus the distribution coefficient ($K_D$) from Example III.

Three different porous UF microsphere lots were produced using a larger scale version of the procedure described in Example I. Each lot was made with a silica sol having a different diameter. Lot 1 was made using Nalcog ® 1115 which has a sol diameter of 5.5 nm. Lot 2 was made using Ludox ® LS which has a sol diameter of 17 nm. Lot 3 was made using Nalcoag ® 1060 which as a sol diameter of 46 nm. FIG. 2 is a plot of polystyrene molecular weight standards versus $K_D$ for these lots. $K_D$ is the distribution coefficient and is calculated using the equation:

$$K_D = \frac{V_R - V_o}{V_m - V_o}$$

where $V_R$ = retention volume of a chromatographic peak $V_o$ = total exclusion volume. The polymer is much larger than the nominal pore size so it cannot diffuse into the pores.

$V_m$ = total liquid volume inside the column and is equal to the sum of pore volume $V_p$ and total exclusion volume, $V_o$.

This equation for $K_D$ (also called $K_{SEC}$ rather indifferently) allows the pore volume to be normalized to the range from 0-1.0. When $K_D = 0$, then $V_R = V_o$ and the substance is excluded from the pores. When $K_D = 1.0$, the substance (small molecule) is totally permeated and explores the entire accessible internal volume within the column, $V_m$.

FIG. 2 clearly illustrates the ability to easily change pore size by changing silica pore size using other classic polymer techniques. This is a significant improvement over existing methods in polymer technology.

EXAMPLE IV

Rigidity and Resilience of UF Microspheres

A 4.6 mm × 250 mm column was packed using UF microspheres produced according to the general procedure given in Example 1 and having a nominal 3 μm diameter. An HPLC pumping system was assembled consisting of a solvent reservoir, pump, and associated stainless steel tubing. An indicator on the pump allowed direct reading of the column inlet pressure.

The pump was first flushed with tetrahydrofuran (THF) and then the column was connected. Approximately 50 mL of mobile phase (THF) was pumped through the column to remove any other solvents. The pump flow rate setting was set to 0.25 $cm^3$/min and the mobile phase was pumped at this constant flow rate for a period of 2-3 min. or until the indicated inlet pressure gave a constant reading. After recording the pressure (in bar) for a setting of 0.25 cm³/min, the flow rate was increased to 50 cm³/min and the pressure reading recorded.

After each reading, the pump flow rate was increased by 0.25 cm³/min and the pressure was recorded until a limit of about 330 bar was reached. Then the flow rate was decreased by 0.25 cm³/min increments and the inlet pressure was recorded for each step. This method generated a data set of ascending and descending pressure reading for each selected flow rate.

The pump was then flushed with a second mobile phase (water) and the experiment was repeated except that readings higher than 350 bar were not take. This limit was nearly reached with a flow rate setting of 1.75 cm³/min.

The pump was flushed with a third mobile phase, acetonitrile (ACN), and the experiment repeated. The upper pressure was nearly reached with a flow rate setting of 4.0 cm³/min.

Figure 3:
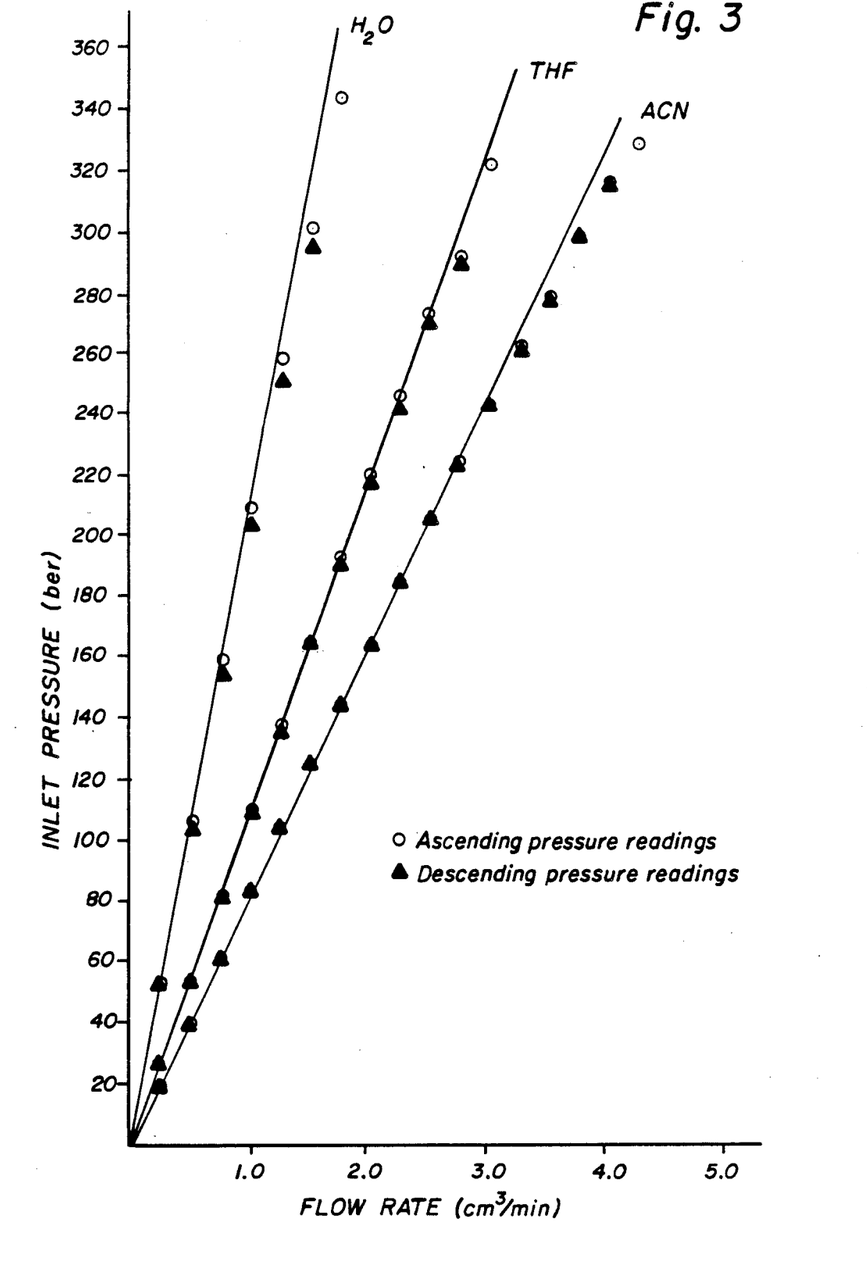
FIG. 3 is a graph of inlet pressure versus flow rate from Example IV.

The experimental results were tabulated according to flow rate, mobile phase, and pressure readings for the first and second runs and are shown in Table 3.

mobile phase due to the column heating up because of the work being done on the system. The lines pass through the origin and this indicates that there is no significant shrinking or swelling occurring in the packed bed; otherwise, a hysteresis effect would be observed and the pressure would be different in the ascending data set than in the descending data set for the same mobile phase when the same flow rate setting was selected. If significant swelling was observed, the pressure would have been very high.

The slopes of the three lines in FIG. 3 are different due to different viscosities of the mobile phases. If the data are corrected for viscosity effects, then the resultant plot should show all points on a single line. For completely rigid microparticles, these plots should yield straight lines passing through the origin. Note that the lines in FIG. 3 are nearly linear at low flow rates and that they indeed do pass through the origin.

The urea formaldehyde microspheres of this invention exhibit very little shrinking or swelling when placed in various organic solvents. In order to demonstrate this, the pressure versus flow rate data can be

TABLE 3

| F Flow Rate (cm³/min) | Mobil Phase: THF P Pressure | | Mobile Phase: H₂O P Pressure | | Mobile Phase: ACN P Pressure | |
|---|---|---|---|---|---|---|
| | Ascending Pressure Reading (bar) | Descending Pressure Reading (bar) | Ascending Pressure Reading (bar) | Descending Pressure Reading (bar) | Ascending Pressure Reading (bar) | Descend Pressure Reading (bar) |
| 0.25 | 26 | 26 | 53 | 53 | 19 | 20 |
| 0.50 | 53 | 53 | 106 | 106 | 40 | 41 |
| 0.75 | 81 | 81 | 159 | 158 | 61 | 62 |
| 1.00 | 110 | 108 | 209 | 209 | 83 | 83 |
| 1.25 | 138 | 137 | 258 | 255 | 104 | 104 |
| 1.50 | 165 | 164 | 301 | 299 | 125 | 125 |
| 1.75 | 193 | 191 | 344 | 341 | 145 | 145 |
| 2.00 | 220 | 219 | | | 165 | 165 |
| 2.25 | 247 | 246 | | | 185 | 185 |
| 2.50 | 274 | 272 | | | 206 | 205 |
| 2.75 | 293 | 294 | | | 225 | 225 |
| 3.00 | 323 | 320 | | | 244 | 244 |
| 3.25 | | | | | 264 | 263 |
| 3.50 | | | | | 280 | 280 |
| 3.75 | | | | | 300 | 300 |
| 4.00 | | | | | 318 | 319 |
| 4.25 | | | | | 330 | 332 |
| 4.00 | | | | | 317 | 317 |
| 3.75 | | | | | 299 | 298 |
| 3.50 | | | | | 279 | 279 |
| 3.25 | | | | | 262 | 261 |
| 3.00 | | | | | 241 | 240 |
| 2.75 | 291 | 293 | | | 223 | 223 |
| 2.50 | 270 | 268 | | | 204 | 205 |
| 2.25 | 243 | 242 | | | 184 | 184 |
| 2.00 | 216 | 215 | | | 164 | 165 |
| 1.75 | 190 | 188 | | | 145 | 145 |
| 1.50 | 162 | 162 | 294 | 295 | 125 | 125 |
| 1.25 | 136 | 135 | 250 | 249 | 104 | 104 |
| 1.00 | 108 | 108 | 204 | 203 | 84 | 84 |
| 0.75 | 81 | 81 | 155 | 155 | 62 | 62 |
| 0.50 | 53 | 53 | 105 | 104 | 41 | 41 |
| 0.25 | 26 | 26 | 53 | 53 | 20 | 20 |

The data were plotted (FIG. 3) with the inlet pressure on the ordinate and flow rate on the abscissa. The open circles indicate data points when the pressure was ascending and the solid triangles when the pressure was descending.

This plot indicates that there is little or no change in the relationship between inlet pressure and flow rate over a wide range. The slopes of the curves are essentially linear in the range from 20 to over 200 bar.

Curvature is to be observed at the higher flow rates which is probably caused by lower viscosity of the normalized to take into account the viscosity effects. If after normalization a pressure versus flow rate curve is linear and independent of the solvent used, then it can be concluded that the urea formaldehyde microspheres did not shrink or swell in water or organic media to any great extent. The flow resistance parameter $\Omega$ (defined below) should be a constant for all solvents and pressures at a given system temperature.

The column inlet pressure can be described by the Darcy equation $$U = \frac{K_o d_p^2 P}{\eta L}$$

where
U = linear velocity
$K_o$ = a constant related to the column permeability
$d_p$ = microsphere particle diameter
P = pressure drop across the column
$\eta$ = viscosity of the solvent
L = column length Since the linear velocity can be obtained by dividing the column length, L, by the time (in seconds) required for a non-sorbed solute to pass through the column:

$$U = \frac{L}{t_o} \text{ in cm/sec}$$

and $t_o$ can be found by dividing the total liquid volume inside the column (pore volume plus interstitial volume between particles), $V_m$, by the flow rate, F, in cm³/min $$t_o = \frac{60 V_m}{F} \times \text{ in seconds}$$

Let $\Omega = 1/K_o$ and become the flow resistance parameter. Then by combining the equations above:

$$U = \frac{L}{t_o} = \frac{LF}{60 V_m} = \frac{d_p^2 P}{\Omega \eta L}$$

$$P = \frac{\Omega \eta L^2 F}{60 V_m d_p^2}$$

If the following convenient chromatographic units are used, then the next equation holds:

P = bar    $\eta$ = Newton sec m$^{-2}$
L = mm    F = cm³/min
$V_m$ = cm³    $d_p$ = microns A packed column having fixed values of $d_p$, L, and $V_m$ will experience a pressure drop which is controlled only by changes in F, N, and temperature. The temperature is assumed to be approximately constant during the experiments. Since the values of $V_m$, $d_p$, and L will not change for a given column, then a new constant, $\epsilon$, can be given as:

$$\epsilon = \frac{6 V_m d_p^2}{L^2}$$

then, $\epsilon P = 106 \eta F$ and a plot of $\epsilon P$ versus $\eta F$ will have a slope which is equal to $\Omega$.

Figure 4:
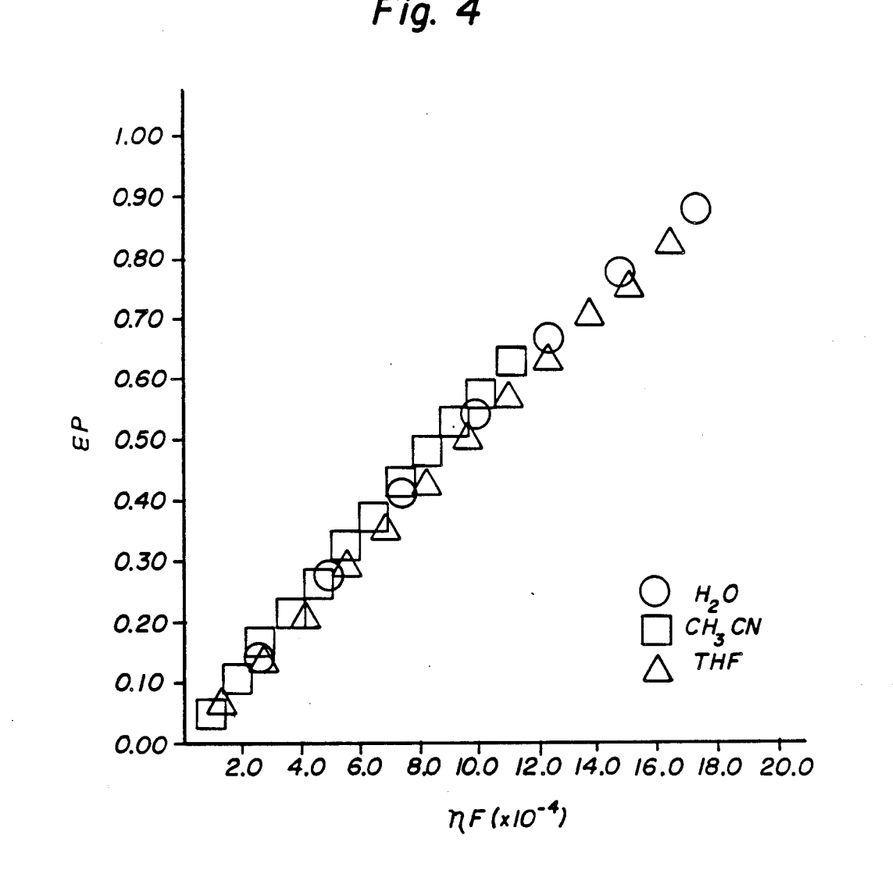
FIG. 4 is a graph of $\epsilon P$ versus $\eta F$ from Example IV.

FIG. 4 is a plot of $\epsilon P$ versus $\eta F$ (data in Tables 4-6). The plot indicates an overlay of data points within experimental error and demonstrates that the urea formaldehyde microspheres do not shrink or swell in the solvents used. The porous urea formaldehyde microspheres of this invention demonstrate surprising rigidity and resistance to swelling in organic solvents compared to other organic chromatographic packings known at this time. The value of $\Omega$ does not change significantly in the range of 0-300 bar with different solvents. The slope of the points in FIG. 4 is approximately 535. A nominal value of 500 for this slope is assumed for spherical silica particles.

TABLE 4

Water as Mobile Phase

| Flow Rate F (cm³/min) | P (bar) | $\epsilon P^*$ | $\eta F^{**}$ ($\times 10^{-4}$) | $\Omega$ |
|---|---|---|---|---|
| 0.25 | 53 | 0.136 | 2.48 | 567 |
| 0.50 | 106 | 0.271 | 4.97 | 545 |
| 0.75 | 159 | 0.407 | 7.45 | 546 |
| 1.00 | 209 | 0.534 | 9.93 | 538 |
| 1.25 | 258 | 0.660 | 12.41 | 532 |
| 1.50 | 301 | 0.770 | 14.90 | 517 |
| 1.75 | 344 | 0.880 | 17.38 | 506 |

*$\epsilon = 2.557 \times 10^{-3}$
**$\eta$ for $H_2O = 0.993 \times 10^{-3}$ N sec/m²

TABLE 5

Acetonitrile as Mobile Phase

| Flow Rate F (cm³/min) | P (bar) | $\epsilon P^*$ | $\eta F^{**}$ ($\times 10^{-4}$) | $\Omega$ |
|---|---|---|---|---|
| 0.25 | 19 | 0.0490 | 0.925 | 530 |
| 0.50 | 40 | 0.103 | 1.850 | 557 |
| 0.75 | 61 | 0.156 | 2.78 | 561 |
| 1.00 | 83 | 0.212 | 3.70 | 573 |
| 1.25 | 104 | 0.266 | 4.63 | 575 |
| 1.50 | 125 | 0.320 | 5.55 | 577 |
| 1.75 | 145 | 0.371 | 6.48 | 573 |
| 2.00 | 165 | 0.422 | 7.40 | 570 |
| 2.25 | 185 | 0.473 | 8.33 | 568 |
| 2.50 | 206 | 0.527 | 9.25 | 570 |
| 2.75 | 225 | 0.575 | 10.18 | 565 |
| 3.00 | 244 | 0.624 | 11.10 | 562 |

*$\epsilon = 2.557 \times 10^{-3}$
**$\eta$ for ACN = $0.37 \times 10^{-3}$ N sec/m²

TABLE 6

Tetrahydrofuran as Mobile Phase

| Flow Rate F (cm³/min) | P (bar) | $\epsilon P^*$ | $\eta F^{**}$ ($\times 10^{-4}$) | $\Omega$ |
|---|---|---|---|---|
| 0.25 | 26 | 0.066 | 1.38 | 478 |
| 0.50 | 53 | 0.136 | 2.75 | 495 |
| 0.75 | 81 | 0.207 | 4.13 | 501 |
| 1.00 | 110 | 0.281 | 5.50 | 511 |
| 1.25 | 138 | 0.353 | 6.88 | 513 |
| 1.50 | 165 | 0.422 | 8.25 | 512 |
| 1.75 | 193 | 0.494 | 9.63 | 513 |
| 2.00 | 220 | 0.563 | 11.00 | 512 |
| 2.25 | 247 | 0.632 | 12.38 | 511 |
| 2.50 | 274 | 0.701 | 13.75 | 510 |
| 2.75 | 293 | 0.749 | 15.13 | 495 |
| 3.00 | 323 | 0.825 | 16.50 | 500 |

*$\epsilon = 2.557 \times 10^{-3}$
**$\eta$ for THF = $0.55 \times 10^{-3}$ N sec/m²

The values of $V_m$, $d_p$ and $L^2$ will not change when the mobile phase is changed and will have a constant value throughout the course of the experiment. For this experiment:

$d_p$ = 3 microns    $V_m$ = 2.96 cm³    L = 250 mm

-continued $$\epsilon = \frac{6 V_m d_p^2}{L^2} = 2.55 \times 10^{-3}$$

EXAMPLE V

Synthesis of Weak Anion Exchange Chromatographic Packing

A. Bromination Reaction 6.0 g of UF microspheres, produced as in Example 1, except that a nominal 1560 nm diameter sol was used, was placed in a three neck 500 mL round bottom flask outfitted with a reflux condenser, stark trap, nitrogen purge tube (10 cm$^3$/min), magnetic stirrer, heating mantle, and a thermometer. 150 mL of ACS grade carbon tetrachloride was added along with 2.0 g of N-Bromosuccimide (NBS) and then 100 mL of Luperson #11, a free radical initiator, was added.

The mixture was stirred with a magnetic stir bar and the resultant slurry was heated to 77° C. In the course of 2.5 hours, the color of the slurry change from a deep orange to white color (~20 min) and then from white to a pumpkin color. The reaction slurry was heated at reflux for 2.5 hours at 77° C. The reaction slurry was then cooled to about 40° C. and filtered using a 1000 mL suction flash through a M-15 sintered glass filter and the cake was then washed successively with two 100 mL portions of tetrahydrofuran (THF) and then with two 100 mL portions of Freon ® TP (Du Pont). The cake was dried to obtain a free flowing pumpkin colored powder and was then placed in a vacuum oven with nitrogen purge (~20 cm$^3$/min) for 20 min. at a temperature of 110° C. and 24" Hg pressure. 4.6 grams of product were recovered.

B. Amine Reaction 4.0 g of the product from the bromination reaction were placed in a 500 mL three neck reaction system, described in the reaction above, which contained 150 mL of neat THF, at about 60° C. 6.0 mL of an amine (3,-3'-Imino-bispropylamine (IBPA) HN[(CH$_2$)$_3$NH$_2$]$_2$, Fw 132.22) was added and refluxed for one hour. The product was filtered in a sintered glass funnel and washed twice with 100 mL THF and then twice with 100 mL Freon ® TP (Du Pont). The cake was dried in the funnel and then transferred to a vacuum oven and dried as above. The product had an unknown structure with the following elemental analysis results(in duplicate): % C=32.35, 32.49; % H=6.42, 6.36; % N=31.93, 31.784; % Br=9.98, 9.94.

C. Chromatographic Results

A column of dimensions 4 mm id. ×80 mm length was slurry packed and placed on a liquid chromatograph (LKB Instruments). The chromatograph was equipped with one pump, a low pressure gradient mixer, an injection valve, and a detector operating at 214 nm wavelength. The "A" mobile phase reservoir contained 0.01 M TRIS, pH 8.0 with 10 mg/L sodium azide (NaN$_3$) and the "B" reservoir contained 0.01 M TRIS, 1.0 M NaCl, pH 8.0, also with 10 mg/L sodium azide. The gradient program was set to pump mobile phase "A" initially until a stable baseline was obtained and then to mix in mobile phase "B" in a linear salt gradient starting with 100% A and ending with 100% B in 20 min. The program then maintained 100% "B" mobile phase for a duration of 5 min. at which time the program then mixed in the "A" mobile phase from 100% "B" to 0% "B" in 1 min. in a linear descending gradient. A contrived sample of three nucleotides (adenosine monophosphate (AMP), adenosine diphosphate (ADP) and adenosine triphosphate (ATP), each at a concentration of 1 mg/mL) was prepared and 25 μL of this sample was injected at gradient time zero. The gradient program was then initiated.

Figure 5:
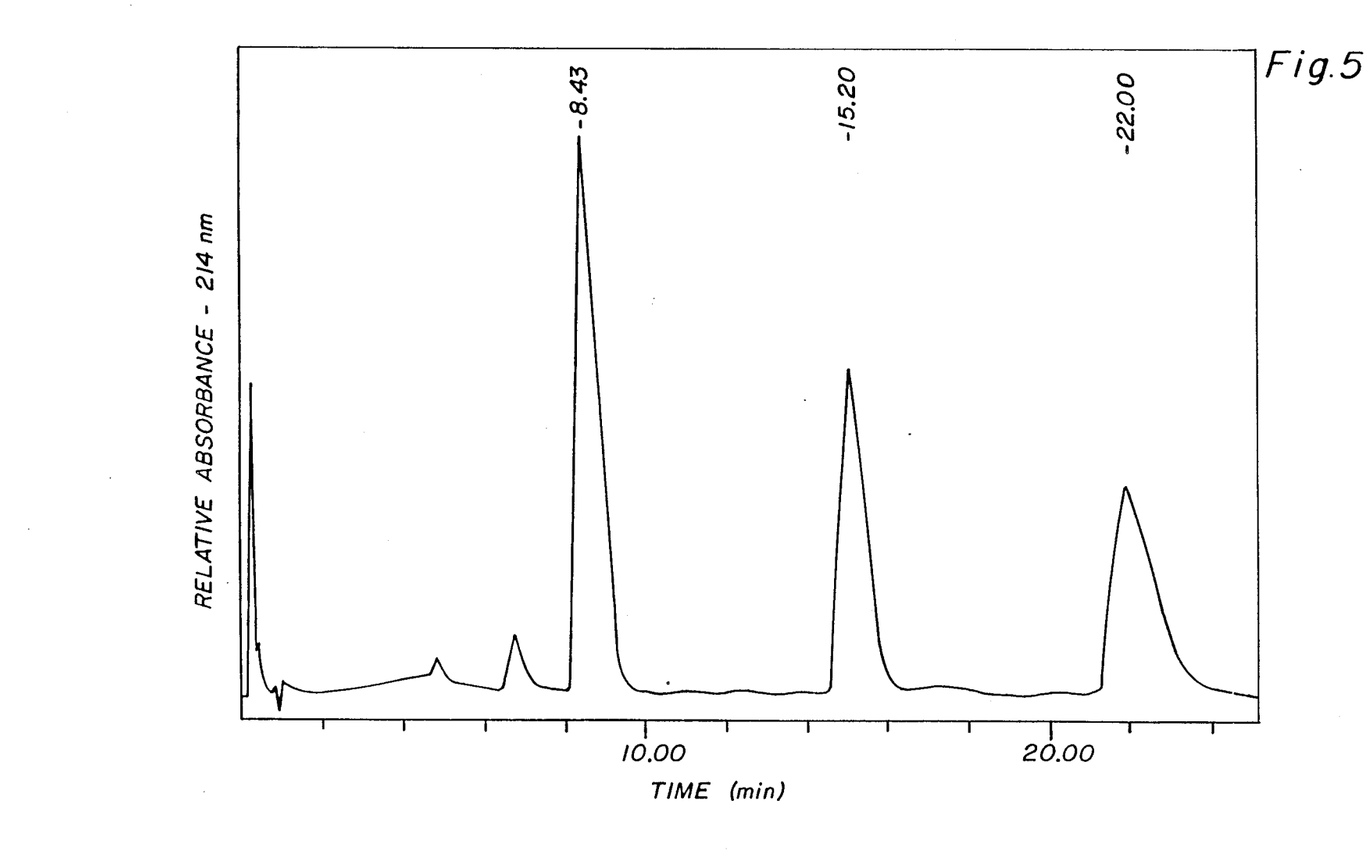
FIG. 5 is a chromatogram of a mixture of nucleotides from Example V.

The analog chromatogram from the detector was digitized and achieved by a Nelson Co. Data System which was controlled by a Hewlett-Packard Model 200 Computer using software from Nelson Co. which was modified by E. I. du Pont de Nemours & Co., Inc. to calculate essential chromatographic parameters. The nucleotide separation is shown in FIG. 5 and indicates that the UF-NH$_2$ microspheres produced by this Example separate ionic substances according to classical theory. k', AMP=11.06, k' ADP=20.71; k' ATP=30.54 where k'=(V$_R$−V$_M$)/V$_M$ where V$_R$=the retention volume and V$_M$=the dead volume inside the column.

EXAMPLE VI

Synthesis of Weak Anion-Exchange Chromatographic Packing

A. Iodoacetate Reaction 300 mL of water and 12.0 g of ascorbic acid, were combined in a 500 mL beaker until the ascorbic acid was dissolved. To this solution was added 6.0 g I—CH$_2$—COONa (sodium salt of iodoacetic acid). The solution was filtered through a 0.2 μm Nalgene sterile filter. The pH was adjusted to pH 1.0 with concentrated H$_3$PO$_4$. 15.0 grams of UF microspheres prepared in a larger scale version of the process described in Example 1 (except Nalcoag ® 1060 sol was used to produce ~50 nm pores) were mixed in by stirring and left to stand at room temperature under nitrogen (~23° C.) for 164 hours.

The above product was filtered and washed three times each with 150 mL of water, then 150 mL THF, then twice with 50 mL methanol then 50 mL Freon ® TP (Du Pont). The cake was air dried in the filter. The dry product was placed in a three neck 250 mL flask which was otherwise identical to the system used in Example V. 100 mL of dry THF was added and a slurry formed by stirring. 2.0 g of 1,1'-carbonyldiimidazole (CDI) was added and the reaction slurry was stirred at room temperature for four hours. The slurry was then filtered and washed twice with 150 mL THF. This product was re-slurried in 100 mL dry THF and placed in a clean 250 mL three neck glass system, otherwise identical to that used in Example V.

4.0 g of tetraethylenepentamine (TEPA) H$_2$N—(CH$_2$)$_2$—NH—(CH$_2$)$_2$—NH(CH$_2$)$_2$—NH(CH$_2$)$_2$—NH$_2$] was added and the reaction slurry was stirred at room temperature for 1.5 hours. The product was filtered in a sintered glass funnel and washed twice each with 150 mL THF, then 50 mL of methanol and finally with 50 mL Freon ® TP (Du Pont) and left to dry in the filter for two hours. About 1 gram of the product was slurried in water and slurry packed in a glass chromatographic column of 5 mm i.d. and 50 mm length. A chromatograph (Pharmacia, FPLC) with a fixed wavelength detector operating at 280 nm was used for the chromatography. The mobile phases were identical to those used in Example V and the gradient program mixed with "A" and "B" mobile phases in a linear gradient from 0% B to 100% B in 30 min. The program then mixed the mobile phases in a linear descending gradient from 100% B to 0% B. The flow rate was maintained constant at 0.5 cm$^3$/min.

Figure 6:
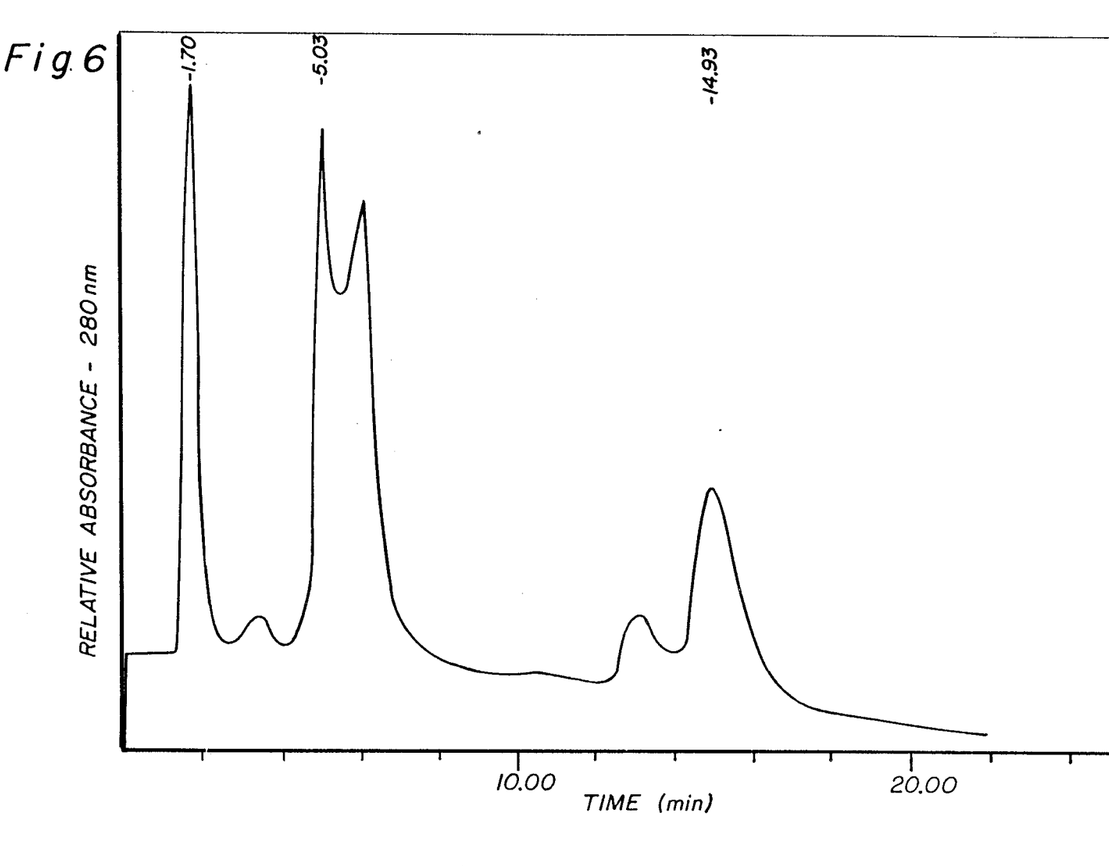
FIG. 6 is a chromatogram of a mixture of proteins from Example VI.

The chromatogram is shown in FIG. 6. The contrived sample consisted of three proteins dissolved in a small quantity (~5 mL) of the "A" buffer, 0.01 M TRIS, pH 8.0 with 10 mg/L NaN$_3$ added. The concentrations were: myoglobin, 2 mg/mL; carbonic anhydrase, 2 mg/mL; ovalbumin, 5 mg/mL. The order of elution was: 1. myoglobin, $V_R=1.70$ cm$^3$; 2. carbonic anhydrase, $V_R=5.03$ cm$^3$; 3. ovalbumin, $V_R=14.93$ cm$^3$.

What is claimed is:

1. A composition comprising a plurality of porous substantially uniform-sized microspheres having an average diameter by number of from 0.5 to 20 microns, the said microspheres being an organic copolymer selected from the group consisting of urea formaldehyde and melamine formaldehyde and (b) defining pores arranged in a uniform three dimensional lattice, said microspheres having a derivatized surface to which is attached functional groups useful in HPLC separations.

2. The composition of claim 1 wherein the microspheres have a uniform density and a uniform pore distribution.

3. The composition of claim 1 which is rigid so as to not swell in organic solvents used in HPLC.

4. The composition of claim 1 which is rigid so as to not shrink in organic solvents used in HPLC.

5. In an apparatus for use in chromatographic separation comprising a region through which materials to be separated are passed, the improvement wherein said region comprises a plurality of uniform-sized porous microspheres having an average diameter of about 0.5 to about 20 microns, substantially all of said microspheres having a diameter ranging from about 0.5 to 1.5 times the average diameter of the microspheres in said region, the said microspheres being an organic copolymer (a) selected from the group consisting of urea formaldehyde and melamine formaldehyde and (b) defining pores arranged in a uniform three dimensional lattice suitable for size exclusion chromatographic applications, said microspheres having a derivatized surface to which is attached functional groups useful in HPLC separations.

6. The apparatus of claim 5 wherein the microspheres have a uniform density and a uniform pore distribution.

7. A composition comprising a plurality of porous substantially uniform-sized microspheres having an average diameter by number of from 0.5 to 20 microns and having a uniform three dimensional lattice, the said microspheres being formed by the steps of:
   a. forming a sol of inorganic colloidal particles in a polar liquid, the colloidal particles having hydroxylated surfaces and being dispersible in the polar liquid;
   b. forming a mixture of the sol with a polymerizable organic material comprising formaldehyde and a second organic material selected from the group consisting of urea and melamine;
   c. polymerizing the organic material in said mixture to cause coacervation of the organic material and said colloidal particles into microparticles having a diameter of about 0.5 to about 20 microns; and
   d. subjecting the microparticles so formed to a solution of a reagent of suitable composition and of sufficient strength to remove all of the inorganic component.

8. A composition produced by the process set forth in claim 7, wherein the inorganic particles are composed of silica, alumina, titania, zirconia, ferric oxide, tin oxide, or antimony oxide.

9. A composition produced by the process set forth in claim 7, wherein the inorganic particles are silica and the reagent is ammonium bifluoride.

10. A composition produced by the process set forth in claim 9, wherein the inorganic colloidal particles are selected to be uniform sized and the mixture of the sol and polymerizable organic material is uniform.

11. A composition produced by the process set forth in claim 7, wherein the inorganic colloidal particles are selected to be uniform sized and the mixture of the sol and polymerizable organic material is uniform.

12. A composition produced by the process set forth in claim 11, wherein the microparticles formed by coacervation are collected, washed and dried prior to being subjected to a reagent.

13. A composition produced by the process set forth in claim 9, wherein the organic microparticles are urea formaldehyde and the process includes the additional step of derivatizing the surface of the microparticles using one of the group consisting of chloroformates, isocyanates, and iodoacetates.

* * * * *